United States Patent
Wollenberg et al.

(10) Patent No.: US 7,468,280 B2
(45) Date of Patent: Dec. 23, 2008

(54) HIGH THROUGHPUT PREPARATION OF LUBRICATING OIL COMPOSITIONS FOR COMBINATORIAL LIBRARIES

(75) Inventors: Robert H. Wollenberg, Orinda, CA (US); Thomas J. Balk, San Francisco, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 0 days.

(21) Appl. No.: 12/072,364

(22) Filed: Feb. 26, 2008

(65) Prior Publication Data

US 2008/0153716 A1 Jun. 26, 2008

Related U.S. Application Data

(63) Continuation of application No. 10/699,510, filed on Oct. 31, 2003, now abandoned.

(51) Int. Cl.
*G01N 33/26* (2006.01)
*C40B 50/00* (2006.01)
*C40B 60/14* (2006.01)

(52) U.S. Cl. ............ 436/60; 436/174; 422/63; 422/67; 422/68.1; 506/23; 506/27; 506/33; 506/37; 506/39; 506/40; 506/43; 508/110

(58) Field of Classification Search .......... 436/60, 436/174, 180, 55; 422/63, 67, 68.1, 100, 422/102, 62; 506/23, 27, 33, 34, 37, 39, 506/40, 43; 508/110
See application file for complete search history.

(56) References Cited

U.S. PATENT DOCUMENTS

| | | | |
|---|---|---|---|
| 5,959,297 A | 9/1999 | Weinberg et al. | |
| 5,985,356 A | 11/1999 | Shultz et al. | |
| 6,004,617 A | 12/1999 | Shultz et al. | |
| 6,030,917 A | 2/2000 | Weinberg et al. | |
| 6,034,775 A | 3/2000 | McFarland et al. | |
| 6,045,671 A | 4/2000 | Wu et al. | |
| 6,087,181 A | 7/2000 | Cong | |
| 6,149,882 A | 11/2000 | Guan et al. | |
| 6,157,449 A | 12/2000 | Hajduk | |
| 6,175,409 B1 | 1/2001 | Nielsen et al. | |
| 6,182,499 B1 | 2/2001 | McFarland et al. | |
| 6,187,164 B1 | 2/2001 | Warren et al. | |
| 6,248,540 B1 | 6/2001 | Weinberg et al. | |
| 6,260,407 B1 | 7/2001 | Petro et al. | |
| 6,265,226 B1 | 7/2001 | Petro et al. | |
| 6,296,771 B1 | 10/2001 | Miroslav | |

(Continued)

FOREIGN PATENT DOCUMENTS

WO  WO 95/13538  5/1995

(Continued)

*Primary Examiner*—Maureen M Wallenhorst
(74) *Attorney, Agent, or Firm*—Claude J. Caroli; M. Carmen & Associates, PLLC

(57) ABSTRACT

A high throughput preparation of a plurality of different lubricating oil compositions for combinatorial libraries and subsequent high throughput screening for lubricant performance is provided. The methods can advantageously be optimized using combinatorial chemistry, in which a database of combinations of lubricating oil compositions are generated. As market conditions vary and/or product requirements or customer specifications change, conditions suitable for forming desired products can be identified with little or no downtime.

31 Claims, 2 Drawing Sheets

U.S. PATENT DOCUMENTS

| | | |
|---|---|---|
| 6,326,090 B1 | 12/2001 | Shultz et al. |
| 6,336,353 B2 | 1/2002 | Matsiev et al. |
| 6,345,528 B2 | 2/2002 | Petro et al. |
| 6,346,290 B1 | 2/2002 | Schultz et al. |
| 6,371,640 B1 | 4/2002 | Hajduk et al. |
| 6,373,570 B1 | 4/2002 | McFarland et al. |
| 6,393,895 B1 | 5/2002 | Matsiev et al. |
| 6,393,898 B1 | 5/2002 | Hajduk et al. |
| 6,395,552 B1 | 5/2002 | Borade et al. |
| 6,401,519 B1 | 6/2002 | McFarland et al. |
| 6,406,632 B1 | 6/2002 | Safir et al. |
| 6,410,331 B1 | 6/2002 | Schultz et al. |
| 6,419,881 B1 | 7/2002 | Weinberg et al. |
| 6,420,179 B1 | 7/2002 | Schultz et al. |
| 6,436,292 B1 | 8/2002 | Petro |
| 6,438,497 B1 | 8/2002 | Mansky et al. |
| 6,440,745 B1 | 8/2002 | Weinberg et al. |
| 6,441,901 B2 | 8/2002 | McFarland et al. |
| 6,461,515 B1 | 10/2002 | Safir et al. |
| 6,468,806 B1 | 10/2002 | McFarland et al. |
| 6,475,391 B2 | 11/2002 | Safir et al. |
| 6,484,567 B1 | 11/2002 | Hajduk et al. |
| 6,491,816 B2 | 12/2002 | Petro |
| 6,508,984 B1 | 1/2003 | Turner et al. |
| 6,519,032 B1 | 2/2003 | Kuebler et al. |
| 6,528,026 B2 | 3/2003 | Hajduk et al. |
| 6,535,284 B1 | 3/2003 | Hajduk et al. |
| 6,535,824 B1 | 3/2003 | Mansky et al. |
| 6,536,944 B1 | 3/2003 | Archibald et al. |
| 6,541,271 B1 | 4/2003 | McFarland et al. |
| 6,553,318 B2 | 4/2003 | Mansky |
| 6,576,906 B1 | 6/2003 | Archibald et al. |
| 6,577,392 B1 | 6/2003 | Nielsen et al. |
| 6,582,116 B2 | 6/2003 | Nielsen |
| 6,605,473 B1 | 8/2003 | Hajduk et al. |
| 6,644,101 B2 | 11/2003 | Hajduk et al. |
| 6,649,413 B1 | 11/2003 | Schultz et al. |
| 6,650,102 B2 | 11/2003 | Hajduk et al. |
| 6,653,138 B1 | 11/2003 | Turner et al. |
| 6,655,194 B2 | 12/2003 | Hajduk et al. |
| 6,658,429 B2 | 12/2003 | Dorsett, Jr. |
| 6,664,067 B1 | 12/2003 | Hajduk et al. |
| 6,668,622 B2 | 12/2003 | Hajduk et al. |
| 6,670,298 B1 | 12/2003 | Weinberg et al. |
| 6,679,130 B2 | 1/2004 | Hajduk et al. |
| 6,681,618 B2 | 1/2004 | Hajduk et al. |
| 6,686,205 B1 | 2/2004 | Shultz et al. |
| 6,690,179 B2 | 2/2004 | Hajduk et al. |
| 2002/0023507 A1 | 2/2002 | Hajduk et al. |
| 2002/0028456 A1 | 3/2002 | Manksy et al. |
| 2002/0029621 A1 | 3/2002 | Hajduk et al. |
| 2002/0032531 A1 | 3/2002 | Mansky et al. |
| 2002/0098332 A1 | 7/2002 | Warren et al. |
| 2002/0148282 A1 | 10/2002 | Hajduk et al. |
| 2002/0155036 A1 | 10/2002 | Hajduk et al. |
| 2002/0164275 A1 | 11/2002 | Wheeler et al. |
| 2003/0007152 A1 | 1/2003 | McFarland et al. |
| 2003/0032198 A1 | 2/2003 | Lugmair et al. |
| 2003/0032205 A1 | 2/2003 | McFarland et al. |
| 2003/0037601 A1 | 2/2003 | Manksy et al. |
| 2003/0037620 A1 | 2/2003 | Mansky |
| 2003/0041653 A1 | 3/2003 | Matsiev et al. |
| 2003/0041671 A1 | 3/2003 | Hajduk et al. |
| 2003/0041672 A1 | 3/2003 | Hajduk et al. |
| 2003/0041676 A1 | 3/2003 | Hajduk et al. |
| 2003/0054740 A1 | 3/2003 | Mansky |
| 2003/0055587 A1 | 3/2003 | Wang et al. |
| 2003/0056576 A1 | 3/2003 | Mansky |
| 2003/0068829 A1 | 4/2003 | Giaquinta et al. |
| 2003/0097871 A1 | 5/2003 | Mansky |
| 2003/0100119 A1 | 5/2003 | Weinberg et al. |
| 2003/0127776 A1 | 7/2003 | Carlson et al. |
| 2003/0133113 A1 | 7/2003 | Hajduk et al. |
| 2003/0138025 A1 | 7/2003 | Archibald et al. |
| 2003/0141613 A1 | 7/2003 | Hajduk et al. |
| 2003/0142309 A1 | 7/2003 | Kuebler et al. |
| 2003/0157721 A1 | 8/2003 | Turner et al. |
| 2003/0161763 A1 | 8/2003 | Erden et al. |
| 2003/0169638 A1 | 9/2003 | Nielsen |
| 2003/0190260 A1 | 10/2003 | Wheeler et al. |
| 2003/0203500 A1 | 10/2003 | Carlson et al. |
| 2003/0211016 A1 | 11/2003 | Dales et al. |
| 2003/0218467 A1 | 11/2003 | Carlson et al. |
| 2003/0219906 A1 | 11/2003 | Giaquinta et al. |
| 2004/0123650 A1 | 7/2004 | Kolosov et al. |
| 2005/0087131 A1 | 4/2005 | Shtein et al. |
| 2006/0247137 A1* | 11/2006 | Boffa .................. 508/110 |
| 2007/0106477 A1* | 5/2007 | Gruter et al. .......... 702/19 |

FOREIGN PATENT DOCUMENTS

| | | |
|---|---|---|
| WO | WO 02/07870 | 1/2002 |
| WO | WO 03/019150 | 3/2003 |

* cited by examiner

HIGH THROUGHPUT PREPARATION OF LUBRICATING OIL COMPOSITIONS FOR COMBINATORIAL LIBRARIES

PRIORITY

This application is a continuation of U.S. patent application Ser. No. 10/699,510, filed Oct. 31, 2003 now abandoned, the contents of which are incorporated herein by reference.

BACKGROUND OF THE INVENTION

1. Technical Field

The present invention relates generally to high throughput preparation of a plurality of different lubricating oil compositions for combinatorial libraries and subsequent high throughput screening for lubricant performance.

2. Description of the Related Art

The use of a combinatorial approach for materials synthesis is a relatively new area of research aimed at using rapid synthesis and screening methods to build libraries of polymeric, inorganic or solid state materials. For example, advances in reactor technology have empowered chemists and engineers to rapidly produce large libraries of discrete organic molecules in the pursuit of new drug discovery, which have led to the development of a growing branch of research called combinatorial chemistry. Combinatorial chemistry generally refers to methods and materials for creating collections of diverse materials or compounds—commonly known as libraries—and to techniques and instruments for evaluating or screening libraries for desirable properties.

Presently, research in the lubricant industry involves individually forming candidate lubricating oil compositions and then performing a macro-scale analysis of the candidate compositions by employing a large amount of the candidate to be tested. Additionally, the methods employed for testing each candidate composition require manual operation. This, in turn, significantly reduces the number of compositions that can be tested and identified as leading lubricating oil compositions.

Drawbacks associated with conventional screening procedures can be seen as follows. For example, governmental and automotive industry pressure towards reducing the phosphorous and sulfur content of lubricating oil compositions used as, for example, passenger car and heavy duty diesel engine oils, is leading to new research to identify oil compositions which can satisfy certain tests such as, for example, oxidation, wear and compatibility tests, while containing low levels of phosphorous and sulfur. In this context, United States Military Standards MIL-L-46152E and the ILSAC Standards defined by the Japanese and United States Automobile Industry Association at present require the phosphorous content of engine oils to be at or below 0.10 wt. % with future phosphorous content being proposed to even lower levels, e.g., 0.08 wt. % by January, 2004 and below 0.05 wt. % by January, 2006. Also, at present, there is no industry standard requirement for sulfur content in engine oils, but it has been proposed that the sulfur content be below 0.2 wt. % by January, 2006. Thus, it would be desirable to decrease the amount of phosphorous and sulfur in lubricating oils still further, thereby meeting future industry standard proposed phosphorous and sulfur contents in the engine oil while still retaining the oxidation or corrosion inhibiting properties and antiwear properties of the higher phosphorous and sulfur content engine oils. In order to accomplish this, a large number of proposed lubricating oil compositions must be tested to determine which compositions may be useful.

Additionally, similar changes in specifications and changing customer needs also drive reformulation efforts in other lubricant applications such as, for example, transmission fluids, hydraulic fluids, gear oils, marine cylinder oils, compressor oils, refrigeration lubricants and the like.

However, as stated above, present research in the lubricant industry does not allow for reformulation to occur in an expeditious manner. As such, there exists a need in the art for a more efficient, economical and systematic approach for the preparation of lubricating oil compositions and screening of such compositions for information correlating to the actual useful properties of the compositions.

Accordingly, it would be desirable to rapidly prepare a plurality of sample candidate lubricating oil compositions utilizing small amounts of each sample. In this manner, a high throughput preparation and subsequent screening of a vast number of diverse compositions can be achieved to identify leading lubricating oil compositions.

SUMMARY OF THE INVENTION

A method for preparing a vast number of diverse lubricating oil compositions and system therefor is provided herein. Accordingly, in one embodiment of the present invention a method for preparing a plurality of different lubricant oil formulations is provided comprising the steps of (a) conducting molecular modeling of at least one base oil of lubricating viscosity and at least one lubricating oil additive to provide leading candidates of the at least one base oil of lubricating viscosity and at least one lubricating oil additive for combination to formulate a leading candidate lubricating oil composition for testing; and (b) containing, under program control, a plurality of leading candidate lubricating oil compositions comprising a major amount of at least one leading base oil of lubricating viscosity candidate and a minor amount of at least one leading lubricating oil additive candidate in varying percentages in a plurality of test reservoirs, wherein the major amount of the at least one leading base oil of lubricating viscosity candidate is greater than about 50 wt. %, based on the total weight of the lubricating oil composition.

In a second embodiment of the present invention, a system for preparing a plurality of lubricant oil compositions, under program control, is provided which comprises:

(a) a supply of a major amount of at least one base oil of lubricating viscosity;

(b) a supply of a minor amount of at least one lubricating oil additive;

(c) a plurality of test reservoirs;

(d) means for conducting molecular modeling of the at least one base oil of lubricating viscosity and the at least one lubricating oil additive to provide leading candidates of the at least one base oil of lubricating viscosity and at least one lubricating oil additive for combination to formulate a leading candidate testing;

(e) combining selected quantities of the major amount of at least one leading base oil of lubricating viscosity candidate with selected quantities of the minor amount of the at least one leading lubricating oil additive candidate to form a plurality of leading candidate lubricating oil composition samples; wherein the major amount of at least one leading base oil of lubricating viscosity candidate is greater than about 50 wt. %, based on the total weight of the lubricating oil composition; and (f) means for dispensing each lubricating oil composition sample in a respective test reservoir.

BRIEF DESCRIPTION OF THE DRAWINGS

Various embodiments are described below with reference to the drawings wherein.

DETAILED DESCRIPTION OF THE PREFERRED EMBODIMENT(S)

Figure 1:
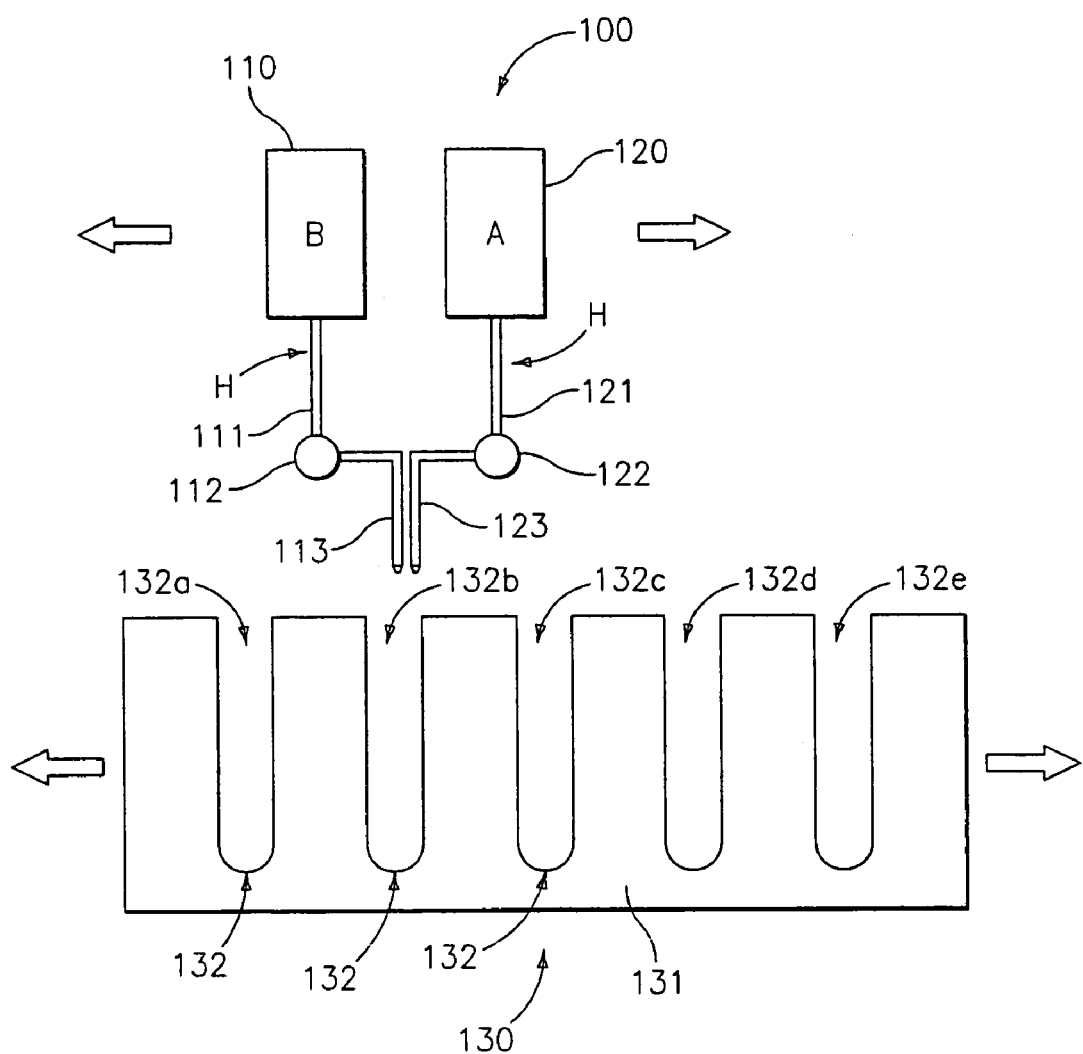
FIG. 1 is a schematic diagram of a system for preparing a plurality of different lubricating oil compositions; and, FIG. 2 is a schematic illustration of a dispensing system of the invention.

The invention is directed to the high throughput preparation of a plurality of different lubricating oil composition samples for subsequent testing for lubricant performance properties. The expression "high throughput" as used herein shall be understood to mean that a relatively large number of different lubricating oil compositions can be rapidly prepared and analyzed. In general, varying quantities of at least one base oil of lubricating viscosity and at least one lubricating oil additive are introduced in respective test reservoirs so that each reservoir contains a different lubricating oil composition. The procedure is advantageously accomplished under program control and is automatically controlled by, for example, a microprocessor or other computer control device. The expression "program control" as used herein shall be understood to mean the equipment used herein in providing the plurality of lubricating oil compositions is automated and controlled by a microprocessor or other computer control device.

The lubricating oil compositions for use in the high throughput preparation method of this invention include as a first component a major amount of base oil of lubricating viscosity, e.g., an amount of greater than 50 wt. %, preferably greater than about 70 wt. %, more preferably from about 80 to about 99.5 wt. % and most preferably from about 85 to about 98 wt. %, based on the total weight of the composition. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered base oil of lubricating viscosity used in formulating lubricating oil compositions for any and all such applications, e.g., engine oils, marine cylinder oils, functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fisher-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The second component of the lubricating oil compositions for use herein is at least one lubricating oil additive. Such additives can be any presently known or later-discovered additive used in formulating lubricating oil compositions. The lubricating oil additives for use herein include, but are not limited to, antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. Greases will require the addition of appropriate thickeners. A variety of the additives are known and commercially available. These additives, or their analogous compounds, can be employed for the preparation of the various lubricating oil compositions herein.

Alternatively, the lubricating oil additive(s) can further contain a diluent oil to form an additive concentrate. These concentrates usually include at least from about 90 wt. % to about 10 wt. % and preferably from about 90 wt. % to about 50 wt. %, of a diluent oil and from about 10 wt. % to about 90 wt. %, preferably from about 10 wt. % to about 50 wt. %, of the foregoing additive(s). Suitable diluents for the concentrates include any inert diluent, preferably an oil of lubricating viscosity such as, for example, a base oil as described hereinbelow, so that the concentrate may be readily mixed with lubricating oils to prepare lubricating oil compositions. Suitable lubricating oils that may be used as diluents can be any oil of lubricating viscosity.

Examples of antioxidants include, but are not limited to, aminic types, e.g., diphenylamine, phenyl-alpha-napthylamine, N,N-di(alkylphenyl) amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic) phenol; sulfur-containing materials, e.g., sulfurized olefins or esters and the like and mixtures thereof.

Examples of antiwear agents include, but are not limited to, zinc dialkyldithiophosphates and zinc diaryldithiophosphates, e.g., those described in an article by Born et al. entitled "Relationship between Chemical Structure and Effectiveness of Some Metallic Dialkyl- and Diaryl-dithiophosphates in Different Lubricated Mechanisms", appearing in Lubrication Science 4-2 Jan. 1992, see for example pages 97-100; aryl phosphates and phosphites, sulfur-containing esters, phosphosulfur compounds, metal or ash-free dithiocarbamates, xanthates, alkyl sulfides and the like and mixtures thereof.

Examples of detergents include, but are not limited to, overbased or neutral detergents such as sulfonate detergents, e.g., those made from alkyl benzene and fuming sulfuric acid; phenates (high overbased or low overbased), high overbased phenate stearates, phenolates, salicylates, phosphonates, thiophosphonates, ionic surfactants and the like and mixtures thereof. Low overbased metal sulfonates typically have a total base number (TBN) of from about 0 to about 30 and preferably from about 10 to about 25. Low overbased metal sulfonates and neutral metal sulfonates are well known in the art.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine, e.g., those disclosed in U.S. Ser. No. 10/402,170, filed Mar. 28, 2003, the contents of which are incorporated by reference herein, and the like and mixtures thereof.

Examples of antifoaming agents include, but are not limited to, polymers of alkyl methacrylate; polymers of dimethylsilicone and the like and mixtures thereof.

Examples of ashless dispersants include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, phosphonoamides, thiophosphonamides and phosphoramides; thiazoles, e.g., 2,5-dimercapto-1,3,4-thiadiazoles, mercaptobenzothiazoles and derivatives thereof; triazoles, e.g., alkyltriazoles and benzotriazoles; copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof. The derivatives of these dispersants, e.g., borated dispersants such as borated succinimides, may also be used. Preferably, the dispersants are polyalkylene succinimides derived from animation of polyalkylene succinic anhydrides with polyalkylene polyamine.

If desired, prior to dispensing the at least one base oil and at least one lubricating oil additive to provide the compositions herein, as discussed hereinbelow, it can be advantageous to conduct molecular modeling of proposed compounds for use in the compositions (i.e., formulations) to determine which compounds may provide potential leading candidate compositions. For example, calculations can be carried out involving such factors as, for example, transition states, bond lengths, bond angles, dipole moment, hydrophobicity, etc, of the compounds. Accordingly, the proposed compounds can be screened to determine, for example, which compounds may perform poorly in an oxidation inhibition process due to a poor ability to trap intermediate peroxides. This can be carried out using known software such as, for example, Quantum Mechanics available from Accelrys (San Diego, Calif.).

Software for the design of test libraries can be used to design the original compound test libraries based on input from the foregoing experimental program(s). This software can be used to efficiently design test libraries that cover the desired experimental space and utilize statistical experimental design methods. Other software can then be used to analyze the data from the experiments and correlate that data with the structure of the compounds and/or compound treatment conditions and/or reaction conditions. Such correlations are often referred to as QSAR software (Quantitative Structure Activity Relations) available from Accelrys (San Diego, Calif.). Such QSAR programs can then be used by the software to design subsequent compound test libraries for further screening.

The use of such QSAR programs can add to the efficiency of screening. As more data is collected, these QSAR programs can become more efficient at developing compounds libraries with increased probability for finding desirable compounds. For example, the compounds analyzed can be formulated into various lubricating oil compositions, as described hereinbelow, and then further analyzed by way of, for example, regression and analysis technologies, using known software, e.g., $C^2$-QSAR available from Accelrys (San Diego, Calif.). In this manner, validation of the data obtained from the molecular modeling can be achieved and then this data can also be stored in a data collector. In this way, new compounds, conceived by one skilled in the art can be checked by the QSAR software to predict their activity prior to their actual synthesis. Additionally, such software tools may be utilized to prioritize a list of possible compounds being considered for synthesis in such a way that one skilled in the art will have a higher probability for success.

Referring now to FIG. 1, a system 100 is shown for preparing a plurality of test samples. Vessel 110 contains a supply of the foregoing base oils of lubricating viscosity B. Vessel 120 contains a supply of additive A, which can be any of the foregoing additives useful for modifying the properties of the base oil so as to provide a lubricating oil composition suitable for the intended use or application. As one skilled in the art would readily appreciate, one or more of vessels 110 and vessels 120 can be used when dispensing more than one base oil and one additive, respectively.

Tubular line 111 is a conduit for communicating the base oil B to nozzle portion 113, from which it can be dispensed into a selected test reservoir, as described below. The amount of base oil dispensed is determined by metering pump 112, which can be computer controlled.

Tubular line 121 is a conduit for communicating lubricating oil additive A to nozzle portion 123, from which it can be dispensed into a selected test reservoir, as described below. The amount of base oil dispensed is determined by metering pump 122, which also can be computer controlled. Computer programs and systems for automatically metering predetermined amounts of materials in accordance with a preselected program control are known in the art and can be used herein.

Nozzles 113 and 123 are preferably in close proximity so that base oil B and additive A can be simultaneously dispensed in a test reservoir. Alternatively, base oil B and additive A can be sequentially added to the test reservoir. The nozzles 113 and 123 can comprise a multichannel pipette or one or more syringe needles.

The vessels 110 and 120 can be under pressure. Optionally, more than two vessels can be employed. Metering pumps suitable for use in the invention are known and commercially available. In the event that highly viscous lubricant base stock or additives are used, the vessels 110 and 120 and/or the tubular lines 111 and 121, metering pumps 112 and 122, and/or nozzles 113 and 123 can be heated to facilitate fluid flow therethrough.

The test frame 130 includes a block 131 of inert material (e.g., glass, ceramic, metal) having a plurality of recesses 132 for receiving the dispensed base oil and additives. The recesses provide test reservoirs wherein each reservoir contains a lubricating oil of a different and predetermined composition, i.e., the percentage and/or type of base oil and/or additives in each composition will vary from one reservoir to another. Optionally, the reservoirs can be individual receptacles (e.g., test tubes) mounted upon a rack, instead of being recesses in a block. While five reservoirs, i.e., recesses 132*a*, 132*b*, 132*c*, 132*d*, 132*e*, are illustrated in FIG. 1, any number of reservoirs can be employed. For example, a 10×10 array of reservoirs would accommodate 100 different lubricating oil formulation samples. It is also contemplated that liners (not shown), e.g., glass or metal such as aluminum, can be inserted into recesses 132*a*, 132*b*, 132*c*, 132*d*, 132*e* prior to depositing the lubricating oil components.

The individual reservoirs are adapted to hold relatively small amounts of lubricating oil samples. The sample size in each reservoir can be no more than about 20 ml, preferably no more than about 15 ml, more preferably no more than about 10 ml and yet more preferably no more than about 5 ml.

The test frame 130 and dispensing nozzles 113 and 123 are movable relative to one another. Although manual movement of the apparatus by an equipment operator is within the purview of the invention, robotic mechanisms with programmable movement are preferred. In one embodiment the test frame 130 is mounted upon a slidable carriage movable in a lateral and/or vertical direction so as to sequentially position a selected recess under the dispensing nozzles 113 and 123. In another embodiment, the nozzles 113 and 123, and optionally the vessels 110 and 120, are slidably movable laterally and/or vertically to accomplish positioning of the nozzles 113 and 123.

In a testing procedure, vessels 110 and 120 are filled with the selected lubricant base oil and additive(s), respectively. The apparatus of system 100 is moved such that dispensing nozzles 113 and 123 are positioned above and in alignment with recess 132*a*. A metered amount of base oil B and a metered amount of additive A are simultaneously dispensed into recess 132*a*. The dispensing nozzles 113 and 123 are thereafter repositioned to be in alignment with the next recess 132*b* and the metered amounts of additive A and/or base oil B are changed in accordance with a predetermined schedule of variation such that the lubricating oil in recess 132*b* has a different percentage composition of additive than that in recess 132*a*. The pattern is repeated as the nozzles 113 and 123 are sequentially aligned with the successive recesses 132*c*, 132*d*, and 132*e* so that each recess has a predetermined composition of lubricating oil.

The components A and B are preferably combined in the reservoirs by mixing, for example, by agitation of the frame 131, static mixing, individual stirring of the contents of the reservoirs (mechanical or magnetic stirring) or by bubbling the reservoir with a gas, e.g., nitrogen.

Optionally, base oil B and additive(s) A can be combined prior to dispensing into the respective reservoirs. For example, a single dispensing nozzle having a mixing chamber can be used, wherein base oil B and additive(s) A are metered into the mixing chamber and then dispensed through the nozzle into the reservoir.

Figure 2:
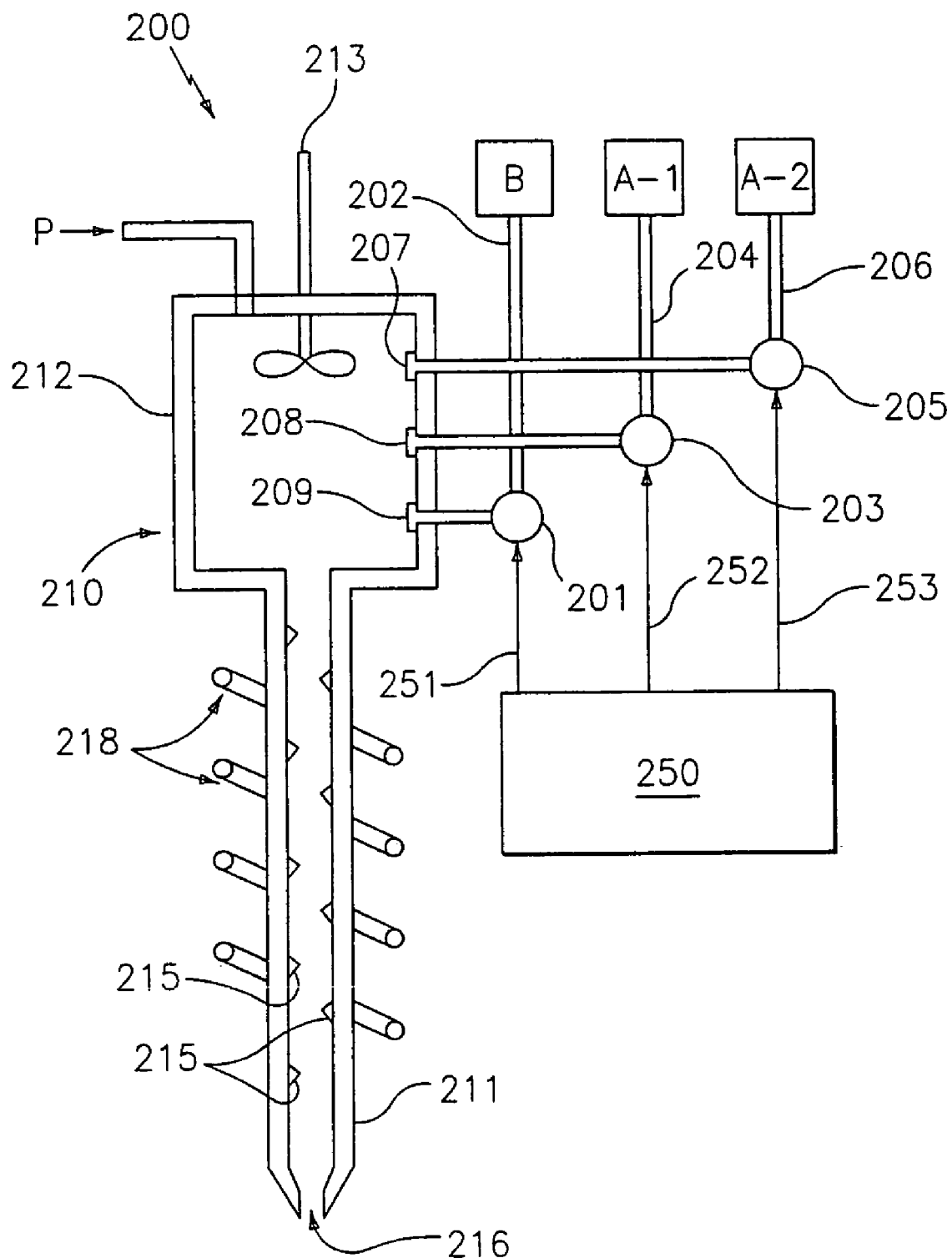

Referring now to FIG. 2, a system 200 for combining and dispensing a lubricating oil composition is schematically illustrated which employs a single nozzle assembly 210 having an elongated injector portion 211 and a mixing chamber 212. The end of injector portion 211 includes an opening 216 through which the lubricating oil composition is ejected into the selected test reservoir.

A conduit 202 conveys a quantity of base oil B through a metering apparatus 201 and into mixing chamber 212. Conduit 204 carries a first additive A-1 through metering apparatus 203 and into mixing chamber 212. Conduit 206 carries a second additive A-2 through metering apparatus 205 and into mixing chamber 212. As one skilled in the art would readily appreciate, while only two additive components A-1 and A-2 are shown, it should be understood that any number of different additives can be individually metered into the nozzle assembly 210. The metering apparatus 201, 203, and 205 are each automatically controlled by control system 250 which preferably includes a microprocessor with the appropriate programming and control connections 251, 252 and 253 for communicating control signals to the respective metering apparatus. Control connections 251, 252 and 253 can be, for example, electrical, optical, pneumatic, or fluidic. The control system 250 determines the composition of the lubricating oil in the mixing chamber 212 by regulating the amounts of the respective lubrication oil components (i.e., base oil B, and additives A-1, A-2, etc.) metered into the nozzle assembly 210.

Preferably the conduits 202, 204, and 206 are terminated with one way valves 207, 208, and 209, respectively, to prevent backflow of the mixing chamber contents in the event that pressure in the mixing chamber 212 exceeds the pressure in the conduits.

The lubricating oil components can be mixed together by various means. For example, mixing unit 213 can be a rotary impeller, or, more preferably, an ultrasonic probe. Optionally, baffles 215 can be incorporated into nozzle assembly 210 for static mixing of the components as they flow through the nozzle assembly.

In the event that high viscosity components are being mixed, a heating unit such as coiled resistance heater 218 can be used to raise the temperature of the components and thereby lower their viscosity to improve fluid flow. Heating units can alternatively be convection units (e.g., hot air blowers), radiant coils, or conduction heaters, and can be used to heat any part of the system 200 including the component supplies (B, A-1, A-2), the conduits (202, 204, 206), the metering apparatus (201, 203, 205), the mixing chamber 212, and/or the injector portion 211 (as shown).

The contents of the mixing chamber 212 can be moved through injector portion 211 by, for example, applying pressure from a pressure source P such as compressed gas. As mentioned above, one-way valves 207, 208, and 209 prevent backflow of the contents into the conduits 202, 204, and 206 if the pressure within the mixing chamber 212 exceeds the pressure within the conduits. Alternatively, the lubricant base oil and additive sources B, A-1 and A-2 can be pressurized and/or the metering apparatus 201, 203 and 205 can provide pumping pressure to move the materials through the system.

The procedure described above provides an array of samples of varying compositions which can be compiled in a data collector, e.g., microprocessor, to provide a combinatorial lubricating oil composition library. The array of samples can then be screened with respect to selected properties and categorized in the combinatorial lubricating oil composition library. For example, the plurality of different lubricating oil compositions can be subjected to further automated or manual screening tests, e.g., storage stability tests, oxidation tests, wear tests, etc., for information correlating to the actual useful properties of the compositions to determine their efficacy. The results of each of the tests can then be compiled in the database as stated above to provide the combinatorial lubricating oil composition library. Alternatively, the system may be electrically connected to a signal data collector comprising a computer microprocessor for system operation and control to collect the data from the various tests over an extended period of time to compile the combinatorial lubricating oil composition library.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A method for preparing a plurality of different lubricating oil compositions, the method comprising:
   (a) conducting molecular modeling of at least one base oil of lubricating viscosity and at least one lubricating oil additive to provide leading candidates of the at least one base oil of lubricating viscosity and at least one lubricating oil additive for combination to formulate a leading candidate lubricating oil composition for testing; and
   (b) containing, under program control, a plurality of leading candidate lubricating oil compositions comprising a major amount of at least one leading base oil of lubricating viscosity candidate and a minor amount of at least one leading lubricating oil additive candidate in varying percentages in a plurality of test reservoirs, wherein the major amount of the at least one leading base oil of lubricating viscosity candidate is greater than about 50 wt. %, based on the total weight of the lubricating oil composition.

2. The method of claim 1, wherein the test reservoirs comprise recesses in a unitary body.

3. The method of claim 1, wherein the test reservoirs comprise individual receptacles.

4. The method of claim 1, wherein the containing step comprises combining, under program control, the major amount of the at least one leading base oil of lubricating viscosity candidate and the minor amount of the at least one leading lubricating oil additive candidate within each respective test reservoir.

5. The method of claim 1, wherein the containing step comprises combining, under program control, the major amount of the at least one leading base oil of lubricating viscosity candidate and the minor amount of the at least one leading lubricating oil additive candidate outside of the test reservoirs.

6. The method of claim 1, wherein the containing step comprises metering predetermined respective amounts of the at least one leading base oil of lubricating viscosity candidate and the minor amount of the at least one leading lubricating oil additive candidate, the metering being automatically controlled by a computer controller.

7. The method of claim 1, wherein the containing step includes mixing of the at least one leading base oil of lubricating viscosity candidate and the minor amount of the at least one leading lubricating oil additive candidate.

8. The method of claim 7, wherein the mixing is accomplished by static mixing or agitation.

9. The method of claim 8, wherein the agitation comprises mechanical stirring.

10. The method of claim 8, wherein the agitation comprises ultrasonic agitation.

11. The method of claim 1, further comprising the step of heating the at least one leading base oil of lubricating viscosity candidate or the at least one leading lubricating oil additive candidate or both.

12. The method of claim 1, wherein the at least one leading base oil of lubricating viscosity candidate is a natural or synthetic oil.

13. The method of claim 1, wherein the major amount of the at least one leading base oil of lubricating viscosity candidate is greater than about 70 wt. %, based on the total weight of the composition.

14. The method of claim 1, wherein the at least one leading lubricating oil additive candidate is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

15. The method of claim 1, wherein the plurality of leading candidate lubricating oil compositions includes at least 100 samples.

16. The method of claim 1, wherein each of the leading candidate lubricating oil composition samples has a volume of no more than about 5 ml.

17. The method of claim 1, further comprising analyzing the plurality of leading candidate lubricating oil compositions.

18. The method of claim 1, wherein the step of molecular modeling is carried out using a computer molecular modeling program.

19. The method of claim 1, further comprising storing information regarding the identity of the leading candidate lubricating oil compositions in the plurality of combinations of leading candidate lubricating oil compositions in a database.

20. A system for preparing a plurality of lubricant oil compositions, under program control, which comprises:
   (a) a supply of a major amount of at least one base oil of lubricating viscosity;
   (b) a supply of a minor amount of at least one lubricating oil additive;
   (c) a plurality of test reservoirs;
   (d) means for conducting molecular modeling of the at least one base oil of lubricating viscosity and the at least one lubricating oil additive to provide leading candidates of the at least one base oil of lubricating viscosity and at least one lubricating oil additive for combination to form a leading candidate lubricating oil composition for testing;
   (e) means of combining selected quantities of the major amount of at least one leading base oil of lubricating viscosity candidate with selected quantities of the minor amount of the at least one leading lubricating oil additive candidate to form a plurality of leading candidate lubricating oil composition samples; wherein the major amount of at least one leading base oil of lubricating viscosity candidate is greater than about 50 wt. %, based on the total weight of the lubricating oil composition; and
   (f) means for dispensing each lubricating oil composition sample in a respective test reservoir.

21. The system of claim 20, wherein the at least one leading base oil of lubricating viscosity candidate is a natural or synthetic oil.

22. The system of claim 20, wherein the major amount of the at least one leading base oil of lubricating viscosity candidate is greater than about 70 wt. %, based on the total weight of the lubricating oil composition.

23. The system of claim 20, wherein the at least one leading lubricating oil additive candidate is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

24. The system of claim 20, wherein the test reservoirs comprise recesses in a unitary body.

25. The system of claim 20, wherein the test reservoirs comprise a plurality of individual receptacles.

26. The system of claim 20, further comprising a computer controller for automatically controlling said means for combining and means for dispensing.

27. The system of claim 20, further comprising a computer controlled metering apparatus for metering selected quantities of the at least one leading base oil of lubricating viscosity candidate and the at least one leading lubricating oil additive candidate for combining to provide the leading candidate lubricating oil composition samples.

28. The system of claim 20, wherein the means for combining comprises a mixer.

29. The system of claim 28, wherein the mixer is one of a baffle-containing static mixer, mechanical stirrer or an ultrasonic mixer.

30. The system of claim 20, further comprising a heater.

31. The system of claim 20, wherein the means for dispensing includes a mixing chamber and a nozzle extending from the mixing chamber, the nozzle terminating in an outlet opening through which the leading candidate lubricant oil composition samples are ejected.

* * * * *